United States Patent [19]

Schmidt

[11] Patent Number: 4,877,919

[45] Date of Patent: Oct. 31, 1989

[54] BUTANE ISOMERIZATION IN THE PRESENCE OF $C_5$ AND $C_6$ HYDROCARBONS

[75] Inventor: Robert J. Schmidt, Rolling Meadows, Ill.

[73] Assignee: UOP, Des Plaines, Ill.

[21] Appl. No.: 185,568

[22] Filed: Apr. 25, 1988

[51] Int. Cl.$^4$ ................................................ C07C 5/13
[52] U.S. Cl. .................................................... 585/748
[58] Field of Search .......................................... 585/748

[56] References Cited

U.S. PATENT DOCUMENTS

| | | | |
|---|---|---|---|
| 2,939,896 | 6/1960 | Myers | 585/748 |
| 3,112,351 | 11/1963 | Hoekstra | 585/748 |
| 3,242,228 | 3/1966 | Riordan et al. | 585/748 |
| 3,789,082 | 1/1974 | Cook et al. | 585/748 |
| 4,113,789 | 9/1978 | Rao et al. | 585/748 |
| 4,333,856 | 6/1982 | Antos | 585/748 |

*Primary Examiner*—Curtis R. Davis
*Attorney, Agent, or Firm*—Thomas K. McBride; John G. Tolomei

[57] ABSTRACT

Butane is isomerized in the presence of substantial quantities of $C_5$ and $C_6$ hydrocarbons using an alumina catalyst having from 0.01 to 0.25 wt. % platinum and 2 to 10 wt. % of a chloride component. The process operates at temperatures ranging from 180°–225° C. (355°–435° F.) and produces a high yield of isobutane while at the same time providing a high level of $C_5$ and $C_6$ hydrocarbon isomerization without a significant increase in yield loss of $C_5$ and higher hydrocarbons. The process can be carried out in a single reaction zone or in a series of reaction zones to increase the production of isoparaffins.

6 Claims, No Drawings

BUTANE ISOMERIZATION IN THE PRESENCE OF $C_5$ AND $C_6$ HYDROCARBONS

BACKGROUND OF THE INVENTION

This invention relates generally to the isomerization of hydrocarbons. This invention relates more specifically to the isomerization of light paraffins using a solid catalyst.

DESCRIPTION OF THE PRIOR ART

High octane gasoline is required for modern gasoline engines. Formerly it was common to accomplish octane number improvement by the use of various lead-containing additives. As lead is phased out of gasoline for environmental reasons, it has become increasingly necessary to rearrange the structure of the hydrocarbons used in gasoline blending in order to achieve high octane ratings. Catalytic reforming and catalytic isomerization are two widely used processes for this upgrading.

A gasoline blending pool normally included $C_4$ and heavier hydrocarbons having boiling points of less than 205° C. (400° F.) at atmospheric pressure. This range of hydrocarbon includes $C_4$–$C_6$ paraffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. Octane improvement can also be obtained by using isomerization to rearrange the structure of the paraffinic hydrocarbons into branch-chained paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branch-chained isoparaffins. Although the $C_6$ and heavier hydrocarbons can be upgraded into aromatics through hydrocyclization, the conversion of $C_6$'s to aromatics creates higher density species and increases gas yields with both effects leading to a reduction in liquid volume yields. Therefore, it is common practice to charge the $C_6$ paraffins to an isomerization unit to obtain $C_6$ isoparaffin hydrocarbons. Consequently, octane upgrading commonly uses isomerization to convert $C_6$ and lighter boiling hydrocarbons and reforming to convert $C_7$ and higher boiling hydrocarbons.

The isomerization of paraffins is a reversible first order reaction. The reaction is limited by thermodynamic equilibrium. It has been generally found that lower temperatures shift the equilibrium of $C_5$ and $C_6$ hydrocarbons toward higher isoparaffin to paraffin ratios. These temperatures are typically in the range of 120°–180° C. (250°–355° F.). When isomerizing butane, its refractory nature demands somewhat higher temperatures usually greater than 170° C. (340° F.) to obtain high equilibrium ratios of isobutane to butane.

A number of catalyst systems have been used in effecting isomerization reactions. Traditional catalyst systems are a hydrochloric acid promoted aluminum chloride system and a supported aluminum chloride catalyst. Recently zeolite catalysts, particularly mordenite, are also finding increased usage due to their decreased sensitivity to sulfur and water. A platinum group metal is usually incorporated into the zeolitic catalyst. All of these catalyst systems are very reactive and can generate undesirable side reactions such as disproportionation and cracking. These side reactions not only decrease the product yield but can form olefinic fragments that combine with the catalyst and shorten its life. One commonly practiced method of controlling these undesired reactions has been to carry out the reaction in the presence of hydrogen. However, high concentrations of hydrogen tend to inhibit the butane isomerization reactions. Therefore, it has been difficult to isomerize butane in the presence of $C_5$–$C_6$ hydrocarbons without sacrificing isobutane yields or obtaining low yields of $C_5$–$C_6$ isoparaffins along with undesirable high gas production and catalyst fouling.

It would be highly desirable to have an isomerization that could convert butane to isobutane in the presence of substantial amounts of $C_5$ and $C_6$ hydrocarbons which also produces high yields of $C_5$ and $C_6$ isoparaffins without significant cracking and light ends production. Such a process is particularly needed due to possible reductions in the allowable vapor pressure for motor fuels which would limit the direct blending of butane in motor fuel. Alternate use of butane as a feed component for alkylation or MTBE production requires isomerization to isobutane. The ability to isomerize butanes in the presence of substantial quantities of $C_5$ and $C_6$ hydrocarbons would avoid the additional capital and operating expenses associated with providing separate processing units for butane and $C_5$–$C_6$ hydrocarbons.

INFORMATION DISCLOSURE

U.S. Pat. No. 2,939,896 issued to Myers discloses a catalyst for the isomerization of $C_4$–$C_6$ hydrocarbons consisting of an activated alumina with 0.01 to 5 wt.% platinum, 0.05 to 8 wt.% chlorine, and at least 0.2 wt.% of a sulfide ion. The catalyst is used in an isomerization process at temperatures in the range of from 320°–490° C. (610°–915° F.).

U.S. Pat. No. 3,242,228 issued to Riordan et al. teaches an isomerization catalyst consisting of an alumina base with 0.01 to 1.0 wt.% platinum, and 2.5 to 7.0 wt.% chlorine. The catalyst is used at process conditions including a liquid hourly space velocity (LHSV) of from 0.5 to 2.0, a hydrogen to hydrocarbon mole ratio within the range of from 0.1:1 to 5.0:1, and a temperature of 150°–200° C. (300°–390° F.) for butane isomerization, or a temperature of 120°–160° C. (250°–320° F.) for $C_5$–$C_6$ isomerization.

U.S. Pat. No. 3,789,082 to Cook et al. is directed to a method for practicing low temperature isomerization using a chlorided platinum-alumina catalyst. The process operates in the presence of a hydrogen chloride promoter in an amount up to 0.1 to 5 wt.% of the feedstock and temperatures in the range of 100°–200° C. (210°–390° F.) for the isomerization of feed streams comprising $C_4$ and/or $C_5$ and/or $C_6$ fractions.

U.S. Pat. No. 4,113,789 issued to Rao et al. mentions the isomerization of $C_5$–$C_6$ hydrocarbons at temperatures ranging from 120°–180° C. (250°–355° F.) and butane at temperatures ranging from 150°–200° C. (300°–390° F.) in the presence of a chlorided platinum alumina catalyst and hydrogen to hydrocarbon ratios in the range of 0.1:1.0 to 1:1.

BRIEF DESCRIPTION OF THE INVENTION

This invention is a process for isomerizing butane in the presence of substantial quantities of $C_5$ and $C_6$ hydrocarbons that achieves high conversion of $C_4$–$C_6$ hydrocarbons, good catalyst stability with a low hydrogen to hydrocarbon ratio, and produces relatively few lighter hydrocarbons. The invention uses a highly active chlorided platinum alumina catalyst in the isomerization reaction which has been surprisingly discovered to isomerize $C_5$ and $C_6$ hydrocarbons at severities and hydrogen concentrations suitable for butane isomerization without substantial cracking or unfavorable paraffin to isoparaffin ratios for the $C_5$-$C_6$ hydrocarbons. Thus, this process allows refiners to obtain increased yields of isobutane and $C_5$ and $C_6$ isoparaffins from facilities that were normally operated to provide either $C_4$ isoparaffins or $C_5$ and $C_6$ isoparaffins.

Accordingly, it is an object of this invention to isomerize butane in the presence of substantial quantities of $C_5$ and $C_6$ hydrocarbons.

It is a further object of this invention to isomerize butane in the presence of a substantial quantity of $C_5$ and $C_6$ hydrocarbons without generating significant amounts of light hydrocarbons.

Another object of this invention is to isomerize butane in existing facilities for $C_5$ and $C_6$ isomerization.

Therefore, in one embodiment, this invention is a process for isomerizing butane in the presence of substantial quantities of $C_5$ and $C_6$ hydrocarbons. The feed stream for the process comprises $C_5$ and $C_6$ hydrocarbons and at least 10 mol% butane. The feed stream has a normal sulfur concentration of less than 0.5 ppm and a water concentration of less than 0.1 ppm. The feed stream is admixed with hydrogen to obtain a hydrogen to hydrocarbon ($H_2$/HC) ratio of less than 1.0. The feed stream and hydrocarbon mixture are contacted in a reaction zone with an isomerization catalyst that comprises alumina and from 0.01 to 0.25 wt.% of platinum and from 2 to 10 wt.% of a chloride component at isomerization conditions including a temperature in a range of from 180°–225° C. (355°–435° F.), a pressure of from 7 barsg to 70 barsg and a space velocity of from 0.1 to 10. A chloride concentration of from 30 to 300 ppm is maintained in the reaction zone. An effluent from the reaction zone is separated into a product stream of $C_4$-$C_6$ hydrocarbons and a fuel gas stream which is removed from the process. The product stream has a $C_4$ isoparaffin/$C_4$ hydrocarbon ratio of at least 20%.

Other aspects of this invention relate to feed stream compositions, effluent stream compositions, reactor configurations, hydrogen concentrations, and catalyst details.

DETAILED DESCRIPTION OF THE INVENTION

The feedstocks that can be used in this invention include hydrocarbon fractions rich in $C_4$-$C_6$ normal paraffins. The term "rich" is defined to mean a stream having more than 50% of the mentioned component. A suitable feed stream will have from 10 to 50% of $C_4$ hydrocarbons with at least 25% of the balance comprising $C_5$-$C_6$ hydrocarbons. Preferred feedstocks are substantially pure normal paraffin streams having 15–40% $C_4$ hydrocarbons with the balance consisting essentially of roughly equal proportions of $C_5$ and $C_6$ paraffins. Other useful feedstocks include light natural gasoline, light straight run naphtha, gas oil condensate, light raffinates, light reformate, light hydrocarbons, and straight run distillates having distillation end points of about 77° C. (170° F.) and containing substantial quantities of $C_4$-$C_5$ paraffins. The feed stream may also contain low concentrations of unsaturated hydrocarbons and hydrocarbons having more than 6 carbon atoms. The concentration of these materials should be limited to 10 wt.% for unsaturated compounds and 20 wt.% for heavier hydrocarbons in order to restrict hydrogen consumption and cracking reactions. The feed may also contain substantial quantities of naphthenic hydrocarbons, the concentration of these components should not normally exceed 25%.

Hydrogen is admixed with the feed in an amount that will provide a hydrogen to hydrocarbon ratio equal to or less than 1.0 at the inlet of the isomerization zone. The hydrogen to hydrocarbon ratio of 1 or less has been found to provide sufficient excess hydrogen for operation of the process. Although no net hydrogen is consumed in the isomerization reaction, the isomerization zone will have a net consumption of hydrogen often referred to as the stoichiometric hydrogen requirement which is associated with a number of side reactions that occur. These side reactions include cracking and disproportionation. Other reactors that will also consume hydrogen include olefin and aromatics saturation. High hydrogen concentrations tend to inhibit the isomerization of butanes by reducing the partial pressure of butane in the vapor phase and thus reducing the rate of reaction, therefore, high hydrogen to hydrocarbon ratios should be avoided. In general, a preferred hydrogen to hydrocarbon ratio is between 0.3 to 0.5.

In most isomerization processes, hydrogen is separated from the effluent and recycled to the isomerization zone. When the hydrogen to hydrocarbon ratio of the reactor effluent is less than 0.05, it is possible to operate the isomerization process without the recycle of hydrogen to the isomerization zone. As the quantity of hydrogen leaving the product recovery section increases, additional amounts of $C_4$ and other product hydrocarbons are taken by the fuel gas stream from the product recovery section. The value of the lost product or the additional expense associated with recovery facilities to prevent the loss of product do not justify operating the process without recycle at effluent hydrogen to hydrocarbon ratios above 0.05.

Hydrogen may be added to the feed mixture in any manner that provides the necessary control for the addition of small hydrogen quantities. Metering and monitoring devices for this purpose are well known by those skilled in the art. As currently practiced, a control valve is used to meter the addition of hydrogen to the feed mixture. The hydrogen concentration in the outlet stream or one of the outlet stream fractions is monitored by a hydrogen monitor and the control valve setting position is adjusted to maintain the desired hydrogen concentration. The direction effluent from the reaction zone contains a relatively high concentration of chlorides that can attack metal components of the monitor. Thus, the monitor preferably measures the concentration of hydrogen in a stream that has undergone caustic treatment for chloride removal such as a stabilizer off gas stream. The hydrogen concentration at the effluent is calculated on the basis of total effluent flow rates.

The hydrogen and hydrocarbon feed mixture is contacted in the reaction zone with an isomerization catalyst. The isomerization catalyst consists of a high chloride catalyst on an aluminum base containing platinum. The aluminum is an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt.% of the platinum. Other platinum group metals may be present in a concentration of from 0.1 to 0.25 wt.%. The platinum component may exist within the final catalytic composite as an oxide or halide or as an elemental metal. The presence of the platinum component in this reduced state has been found most suitable for this process.

The catalyst also contains a chloride component. The chloride component termed in the art "a combined chloride" is present in an amount from about 2 to about 10 wt.% based upon the dry support material. The use of chloride in amounts greater than 5 wt.% have been found to be the most beneficial for this process.

There are a variety of ways for preparing the catalytic composite and incorporating the platinum metal and the chloride therein. The method that has shown the best results in this invention prepared the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the halogen. Halogen may also be added to the carrier material by contacting the calcined carrier material with an aqueous solution of the halogen acid such as hydrogen chloride, hydrogen fluoride, or hydrogen bromide.

It is generally known that high chlorided platinum-alumina catalysts of this type are highly sensitive to sulfur and oxygen-containing compounds. Therefore, the feedstock must be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$-$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feed stream by hydrotreating. A variety of commercial dryers are available to remove water from the feed components. Adsorption processes for the removal of sulfur and water from hydrocarbon streams are also well known to those skilled in the art.

Operating conditions within the isomerization zone are selected to provide a good overall selectivity of isoalkane product from the feed components. Temperatures within the reaction zone will range from about 180°–225° C. (355°–425° F.). Lower reaction temperatures in this range favor equilibrium mixtures of $C_5$ and $C_6$ isoalkanes versus normal pentane and hexane. However, higher temperatures in the range of 200°–225° C. (390°–435° F.) are preferred since they offer a significant increase in isobutane production with only a minimal decrease in the ratio of $C_5$ and $C_6$ isoalkanes to pentane and hexane. Of course, the most suitable temperature will depend on the composition of the feed. When the overall quantities of $C_4$ hydrocarbons are higher, the preferred higher temperatures will offer the greatest overall production of isoalkanes. For feeds having fewer $C_4$'s, temperatures of between 180°–205° C. (355°–400° F.) may be most advantageous.

The reaction zone may be maintained over a wide range of pressures. Pressure conditions in the isomerization of $C_4$-$C_5$ paraffins range from 7 barsg to 70 barsg. Preferred pressures for this process are in the range of from 20 barsg to 30 barsg. The feed rate to the reaction zone can also vary over a wide range. These conditions include liquid hourly space velocities ranging from 0.5 to 12 hr.$^{-1}$, however, space velocities between 1 and 4 hr.$^{-1}$ are preferred.

Operation of the reaction zone also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

The reaction can be carried out in multiple reaction stages. A typical system will have a two-reactor system comprising a first stage reactor and a second stage reactor. The catalyst used in the process is usually distributed equally between the different reaction stages. It is not necessary that the reaction be carried out in two or more reactors but the use of at least two reactors confers several benefits on the process. The use of two reactors and specialized valving (not shown) allows partial replacement of the catalyst system without taking the isomerization unit off stream. For the short periods of time during which replacement of catalyst may be necessary, the entire flow of reactants may be processed through only one reaction vessel while catalyst is replaced in the other. The two reaction zones can also be used to maintain lower catalyst temperatures. This is accomplished by having any exothermic reaction such as hydrogenation of unsaturates performed in a first reaction vessel with the rest of the reaction carried out in a final reactor stage at lower temperature conditions. Therefore, the first reaction zone can operate at a somewhat higher temperature, of about 200°–225° C., (390°–435° F.) which favors the isomerization of butanes and the lower temperature of the second reaction zone will increase the $C_5$ and $C_6$ isoparaffin to paraffins ratios by a small amount without reversing the isobutane yield. When two reaction zones are used in this manner, the last reaction zone in the series can be operated at a temperature below 190° C. (375° F.). When two reaction zones are used at different temperatures, the isobutane to $C_4$ hydrocarbon ratio in the product stream will usually exceed 40%.

The process of this invention will include separation facilities for recovering the isomerization product. At minimum, the separation facilities divide the reaction zone effluent into a product stream comprising $C_4$ and heavier hydrocarbons and a gas stream which is made up of lighter hydrocarbons and hydrogen. Suitable designs for rectification columns and separator vessels are well known to those skilled in the art. The separation section may also include facilities for recovery of normal alkanes. Normal alkanes recovered from the separation facilities may be recycled to the isomerization reaction zone to increase the conversion of normal alkanes to isoalkanes. A typical arrangement for the separation facilities will include a stabilizer section that receives the effluent from an isomerization reactor and directs it to a stabilizer column. The stabilizer column is operated to deliver a bottoms fraction containing $C_4$ and heavier hydrocarbon and an overhead fraction of $C_3$ hydrocarbons and lighter boiling compounds. Products taken from the bottom of the column can be cooled by heat exchange with the reactor effluent before it enters the column. $C_3$ and lighter hydrocarbons and any excess hydrogen from the reaction zone are taken overhead from stabilizer column, cooled in a condenser 58, and separated into a gas stream and reflux that returns to the separation column.

Net gas from the separator column will ordinarily enter a scrubber section that contacts the gas with a suitable treatment solution for neutralizing and/or removing acidic components that may have originated with the chloride addition to the isomerization zone and may be present in the gas stream. Typically, the treatment solution will be a caustic that is pumped into a loop around a contacting vessel. After treatment in the scrubber section, the set gas is removed from the process and usually put to use as a fuel.

EXAMPLE I

In this example, roughly equal weight mixture of $C_4$, $C_5$ and $C_6$ normal paraffins were passed through a bed of isomerization catalyst at a liquid hourly space velocity of 2, a pressure of 450 psig, a hydrogen to hydrocarbon ratio of 1.0 and in the presence of 200 ppm of a chloride promoter. The catalyst consisted of an alumina catalyst having 0.25 wt.% platinum and 5.5 wt.% chlorine.

The catalyst was prepared by vacuum impregnating an alumina base in a solution of chloroplatinic acid, 2% hydrochloric acid, and 3.5% nitric acid in a volume ratio of 9 parts solution to 10 parts base to obtain a peptized base material having a platinum to base ratio of approximately 0.9. The resulting mixture was cold-rolled for approximately 1 hour and evaporated until dry. Afterward, the catalyst was oxidized and the chloride content adjusted by contact with a 1M hydrochloric acid solution at 525° C. (975° F.) at a rate of 45 cc/hour for 2 hours. The catalyst was then reduced in electrolytic hydrogen at 565° C. (1050° F.) for 1 hour and was found to contain approximately 0.25 wt.% Pt and approximately 1 wt.% chloride. Impregnation of active chloride to a level of approximately 5.5 wt.% was accomplished by sublimating alumina chloride with hydrogen and contacting the catalyst with the sublimated alumina chloride.

The experiment began with an initial reactor temperature for 170° C. (340° F.). As the experiment progressed, the reactor temperature was increased in stages with each stage being held a minimum of 24 hours until the process became lined out and data could be collected. The results of the experiment are summarized in Table 1.

TABLE 1

| LHSV, $hr^{-1}$ | T, °C. | Product Ratios, % | | | $C_5$+Yield, wt. % |
|---|---|---|---|---|---|
| | | $iC_4/C_4P$ | $iC_5/C_5P$ | 2,2-DMB/ $C_6P$ | |
| 2 | 170 | 17 | 76 | 28 | 100 |
| 2 | 185 | 31 | 75.5 | 27.5 | 97 |
| 2 | 200 | 42 | 74.5 | 27 | 92 |
| 2 | 215 | 51 | 73.5 | 26 | 88 |
| 2 | 225 | 55 | 72.5 | 25 | 80 |

The Products ratios shows that as the reactor temperature of the reactor was increased over 180° C. (355° F.), significant isobutane product was produced. This isobutane production was accompanied by a very high product ratio for $C_5$ isoparaffins to $C_5$ aliphatic paraffins and relatively high product ratio for $C_6$ isoparaffins to $C_6$ aliphatic hydrocarbons. For this process, these ratios will usually exceed 70% for isopentane and 25% for 2,2-dimethylbutane. Monitoring of $C_5$ yield also shows that little of the desired hydrocarbons were lost to cracking or disproportionation. Isobutane production increased dramatically at the temperature was raised while the corresponding iso-$C_5$ and iso-$C_6$ product ratio dropped only slightly. Although $C_5$ yield started to drop somewhat as the reactor approaches its highest temperatures, the small differential loss of yields was more than offset by the benefits of obtaining higher isobutane yield with relatively constant isoparaffin/-paraffin product ratios for the $C_5$ and $C_6$ hydrocarbons.

EXAMPLE II

As a comparison, the same experiment was repeated with a different commercial isomerization catalyst. The experiment was conducted in essentially the same manner as described under Example I.

The catalyst consisted of an alumina mordenite blend having a surface of 622 m²/g and 0.30 wt.% platinum. The catalyst was prepared by mixing a 9:1 weight ratio of mordenite and alumina with an acidified peptization solution and extruding the catalyst into a desired shape. After drying, the extrudate was contacted with an acidic aqueous solution containing 10 wt.% HCl and 10 wt.% $NH_4Cl$ at 60° C. (140° F.) for 120 minutes at a solution to zeolite weight ratio of 25:1. Following drying and calcination, the composite was impregnated to the stated platinum level and calcined again.

The results of the experiment are listed in Table 2. For the comparison catalyst, significant isobutane production was not obtained until the reactor temperature was increased to 260° C. (500° F.). As the temperature was increased further, isobutane product ratios as well as product ratios for $C_5$ and $C_6$ isoparaffins increased. The product ratios for the $C_5$ and $C_6$ isoparaffins were significantly lower at all temperatures tested. It was only at the highest temperature levels that the isobutane/butane product ratio matched the lowest isobutane products ratios obtained with the process of this invention; however, the higher isobutane ratio for the comparison was accompanied by an unacceptable yield of $C_5$ and higher isoparaffins.

TABLE 2

$C_4/C_5/C_6$ ISOMERIZATION
Using an Equal Wt. Mixture of
Feed Components by Carbon Number

| LHSV, $hr^{-1}$ | T, °C | Product Ratios, % | | 2,2-DMB/ $C_6P$ | $C_5+$ Yield wt. % |
|---|---|---|---|---|---|
| | | $iC_4/C_4P$ | $iC_5/C_5P$ | | |
| 2 | 260 | 7 | 60 | 14 | 100 |
| 2 | 260 | 8 | 62 | 14.5 | 99 |
| 2 | 282 | 15 | 68 | 18 | 89 |
| 2 | 307 | 31 | 67 | 18 | 65 |
| 1 | 282 | 22 | 67 | 18 | 82 |

These examples demonstrate the ability of this process to isomerize butane in the presence of substantial $C_5$ and $C_6$ hydrocarbons while simultaneously obtaining high product ratios of $C_5$ and $C_6$ isoparaffins to normal paraffins without the loss of valuable $C_5$ and $C_6$ hydrocarbons to light hydrocarbons. The presentation of these specific examples is not intended to restrict the scope of the invention or the appended claims.

What is claimed is:

1. A process for isomerizing $C_4$ normal hydrocarbons in the presence of $C_5$ and $C_6$ normal hydrocarbons, said method comprising:
   (a) charging a feed stream to a reaction zone, said feed stream comprising $C_4$-$C_6$ hydrocarbons and having at least 10 mol% $C_4$ hydrocarbons and at least 25 mol% $C_5$-$C_6$ hydrocarbons;
   (b) adding hydrogen to said feed stream at a hydrogen to hydrocarbon ratio of less than 0.5;
   (c) contacting said feed stream and hydrogen in said reaction zone with an isomerization catalyst consisting of alumina, 0.01 to 0.25 wt.% platinum and from 2 to 10 wt.% of a chloride component at isomerization conditions including a temperature in the range of from 200°-225° C. (392°-435° F.), a pressure of from 7 to 70 barsg and a space velocity of from 0.1 to 10;
   (d) maintaining a chloride concentration in the reaction zone of from 30 to 300 ppm; and
   (e) recovering an effluent stream from the reaction zone comprising an isomerate product stream having a $C_4$ isoparaffin/$C_4$ hydrocarbon ratio of at least 20%.

2. The process of claim 1 wherein the feed stream comprises from 10-50 mol.% $C_4$ hydrocarbons and approximately equal proportions of $C_5$ and $C_6$ hydrocarbons.

3. The process of claim 1 wherein said product stream has a ratio of $C_5$ isoparaffin to $C_5$ aliphatic hydrocarbons of at least 70% and a ratio of 2,2-dimethylbutane to $C_6$ aliphatic hydrocarbons of at least 25%.

4. A process for isomerizing $C_4$ normal hydrocarbons in the presence of $C_5$ and $C_6$ normal hydrocarbons, said method comprising:
   (a) charging a feed stream to a first reaction zone, said feed stream comprising $C_4$-$C_6$ hydrocarbons and having at least 10 mol% $C_4$ hydrocarbons and at least 25 mol% $C_5$ and $C_6$ hydrocarbons;
   (b) adding hydrogen to hydrocarbon ratio of less than 0.5;
   (c) contacting said feed stream and hydrogen in a first reaction zone with an isomerization catalyst, and at isomerization conditions including a temperature in the range of from 200°-225° C. (390°-435° F.), a pressure of from 20 barsg to 30 barsg and a space velocity of from 1 to 4, while maintaining a chloride concentration of from 30 to 300 ppm in said reaction zone, wherein said isomerization catalyst consisting of alumina, 0.01 to 0.25 wt.% platinum and from 2 to 10 wt.% of a chloride component;
   (d) passing at least a portion of a first effluent stream from said first reaction zone to a second reaction zone and contacting said effluent with said isomerization catalyst at isomerization conditions including a temperature in the range of from 180°-205° C. (355°-400° F.), a pressure of from 7 to 30 barsg and a space velocity of from 0.1 to 4 while maintaining a chloride concentration and said reaction zone of from 30 to 300 ppm; and
   (e) recovering a second effluent stream from said second reaction zone having a ratio of $C_4$ isoparaffins to paraffins of at least 40%, a ratio of $C_5$ isoparaffins of $C_5$ aliphatic hydrocarbons of at least 70%, a ratio of $C_6$ isoparaffins to $C_6$ aliphatic hydrocarbons of at least 25% and a hydrogen to hydrocarbon ratio of less than 0.3.

5. The process of claim 4 wherein the said second effluent has a hydrogen to hydrocarbon ratio of less than 0.05.

6. The process of claim 5 wherein said feed stream comprises from 10-50 mol.% $C_4$ hydrocarbons and approximately equal proportions of $C_5$ and $C_6$ hydrocarbons.

* * * * *